United States Patent
Ishikawa et al.

(10) Patent No.: US 6,860,926 B2
(45) Date of Patent: Mar. 1, 2005

(54) FLUORINE-CONTAINING COMPOUND, AND WATER AND OIL REPELLENT COMPOSITION

(75) Inventors: Minako Ishikawa, Kanagawa (JP); Takashige Maekawa, Kanagawa (JP); Ryuji Seki, Kanagawa (JP); Shoji Furuta, Kanagawa (JP); Kazuya Oharu, Kanagawa (JP)

(73) Assignee: Asahi Glass Company, Limited, Tokyo (JP)

( * ) Notice: Subject to any disclaimer, the term of this patent is extended or adjusted under 35 U.S.C. 154(b) by 353 days.

(21) Appl. No.: 09/976,435

(22) Filed: Oct. 15, 2001

(65) Prior Publication Data

US 2002/0060304 A1 May 23, 2002

Related U.S. Application Data

(63) Continuation of application No. PCT/JP01/01425, filed on Feb. 26, 2001.

(30) Foreign Application Priority Data

Feb. 29, 2000 (JP) ........................................ 2000-054069

(51) Int. Cl.$^7$ ....................... C07C 69/63; C07C 311/24; C09K 3/18
(52) U.S. Cl. ...................... 106/2; 252/8.62; 427/393.4
(58) Field of Search ............................ 106/2; 252/8.62; 427/393.4

(56) References Cited

U.S. PATENT DOCUMENTS

| 3,509,061 A | 4/1970 | Zisman et al. |
| 6,251,984 B1 | 6/2001 | Shimada et al. |
| 6,271,283 B1 | 8/2001 | Shimada et al. |

FOREIGN PATENT DOCUMENTS

| JP | 9-323956 | | 12/1997 |
| JP | 10-168383 A | * | 6/1998 |
| WO | WO 97/11135 | | 3/1997 |
| WO | WO 99/05345 | | 2/1999 |
| WO | WO 01/64619 A1 | | 9/2001 |

* cited by examiner

Primary Examiner—Anthony J. Green
(74) Attorney, Agent, or Firm—Oblon, Spivak, McClelland, Maier & Neustadt, P.C.

(57) ABSTRACT

The following fluorine-containing compound is presented which is capable of providing dry soil resistance when incorporated to a water and oil repellent.

$R^{f1}R^2OCOCH_2CHR^1COOR^3R^{f2}$ (wherein each of $R^{f1}$ and $R^{f2}$ which are independent of each other, is a $C_{3-22}$ polyfluoroalkyl group, $R^1$ is a hydrogen atom or a $C_{1-10}$ alkyl group, and each of $R^2$ and $R^3$ which are independent of each other, is a $C_{1-4}$ alkylene group, etc.).

8 Claims, No Drawings

FLUORINE-CONTAINING COMPOUND, AND WATER AND OIL REPELLENT COMPOSITION

This Appn is a con of PCT/JP01/01425, Feb. 26, 2001.

TECHNICAL FIELD

The present invention relates to a useful novel fluorine-containing compound which is capable of providing dry soil resistance, etc., when incorporated to a water and oil repellent, etc., and a water and oil repellent composition.

BACKGROUND ART

Fluorine-containing compounds are widely used as additives to impart various properties such as a lubricating property, a penetration property, a film-forming property and a hand modification. For example, there is a specific fluorine-containing compound to be incorporated in a water and oil repellent composition, whereby a coating film excellent in water and oil repellency can be obtained even by curing at a low temperature (JP-A-10-81873), or a specific fluorine-containing compound to be incorporated in a composition which is capable of imparting dust soil resistance to fiber (WO96-38622).

However, when a conventional fluorine-containing compound is used as an additive, there has been a problem such that precipitates tend to form depending upon the ionic nature of the main agent of e.g. a water and oil repellent, or there has been a problem such that it can not be used repeatedly depending upon the treating method.

The present invention has an object to provide a novel fluorine-containing compound which can be used as an additive irrespective of the ionic nature of the main agent of e.g. a water and oil repellent, and which is capable of providing dry soil resistance, particularly when incorporated to a water and oil repellent. Further, it has an object to provide a water and oil repellent composition comprising such a fluorine-containing compound.

DISCLOSURE OF THE INVENTION

The present invention provides a fluorine-containing compound represented by the following formula 1 (hereinafter referred to also as the compound 1, the same applies in other cases).

Here, the symbols in the formula 1 represent the following meanings.

$R^{f1}$, $R^{f2}$: each independently, a $C_{2-22}$ polyfluoroalkyl group;

$R^1$: a hydrogen atom or a $C_{1-10}$ alkyl group;

$R^2$, $R^3$: each independently, a $C_{1-4}$ alkylene group or —$R^4$—$NR^5$—$SO_2$— (wherein $R^4$ is a $C_{1-4}$ alkylene group, and $R^5$ is a $C_{1-4}$ alkyl group);

$$R^{f1}—R^2—OCO—CH_2CHR^1—COO—R^3—R^{f2} \quad \text{Formula 1}$$

Further, the present invention provides a water and oil repellent composition comprising a polymer (A) having fluorine atoms and the compound 1.

BEST MODE FOR CARRYING OUT THE INVENTION

In the compound 1, each of $R^{f1}$ and $R^{f2}$ which are independent of each other, represents a $C_{2-22}$ polyfluoroalkyl group (hereinafter referred to as a $R^f$ group). The $R^f$ group means a group having at least two hydrogen atoms in an alkyl group substituted by fluorine atoms. The carbon number in the $R^f$ group is preferably from 4 to 16. Further, the $R^f$ group may have a linear structure or a branched structure, preferably a linear structure. In the case of a branched structure, it is preferred that the branched moiety is present at a terminal portion of the $R^f$ group, and the branched moiety is a short chain having a carbon number of from about 1 to about 3.

The $R^f$ group may contain other halogen atoms than fluorine atoms. As such other halogen atoms, chlorine atoms are preferred. Further, an etheric oxygen atom may be inserted between a carbon-carbon bond in the $R^f$ group. The number of fluorine atoms in the $R^f$ group is preferably at least 60%, particularly preferably at least 80%, when represented by [(number of fluorine atoms in the $R^f$ group)/(number of hydrogen atoms contained in an alkyl group corresponding to the $R^f$ group having the same carbon number)]×100(%).

Further, the $R^f$ group is preferably a group having all of hydrogen atoms in an alkyl group substituted by fluorine atoms, i.e. a perfluoroalkyl group. The carbon number of such a perfluoroalkyl group is preferably from 4 to 16. The perfluoroalkyl group may have a linear structure or a branched structure, preferably a linear structure.

The following groups may be mentioned as specific examples of the $R^f$ group.

$F(CF_2)_2$—, $F(CF_2)_3$—, $F(CF_2)_4$—, $F(CF_2)_5$—, $F(CF_2)_6$—, $F(CF_2)_8$—, $F(CF_2)_9$—, $F(CF_2)_{10}$—, $F(CF_2)_{12}$—, $F(CF_2)_{13}$—, $F(CF_2)_{14}$—, $F(CF_2)_{16}$—, $H(CF_2)_8$—, $(CF_3)_2CF(CF_2)_6$—, $(CF_3)_2CF(CF_2)_8$—, $Cl(CF_2)_8$—, $F(CF_2)_3OCF(CF_3)$—, $F(CF_2)_2[CF_2OCF(CF_3)]_2$—, $F(CF_2)_3OCF(CF_3)O(CF_2)_2$—.

In the compound 1, $R^{f1}$ and $R^{f2}$ may be the same or different, preferably the same.

$R^1$ is a hydrogen atom or a $C_{1-10}$ alkyl group, preferably a hydrogen atom.

Each of $R^2$ and $R^3$ which are independent of each other, is a $C_{1-4}$ alkylene group or —$R^4$—$NR^5$—$SO_2$— (wherein $R^4$ is a $C_{1-4}$ alkylene group, and $R^5$ is a $C_{1-4}$ alkyl group). $R^2$ and $R^3$ may be the same or different, preferably the same. $R^2$ and $R^3$ are preferably the same $C_{1-4}$ alkylene groups, particularly preferably ethylene groups.

The following groups may be mentioned as specific examples of —$R^4$—$NR^5$—$SO_2$—. Further, in the compound 1, $R^4$ bonds to the oxygen atom.

—$(CH_2)_2N(CH_3)SO_2$—, —$(CH_2)_2N(C_2H_5)SO_2$—, —$(CH_2)_2N(C_4H_9)SO_2$—, —$(CH_2)_3N(CH_3)SO_2$—, $CH_2CH(CH_3)CH_2N(CH_3)SO_2$—.

As specific examples of the compound 1, the following compounds may, preferably, be mentioned. In the following compounds, it is more preferred that the $R^f$ group moiety has a linear structure.

$F(CF_2)_8(CH_2)_2OCO(CH_2)_2COO(CH_2)_2(CF_2)_8F$ Compound A $F(CF_2)_8(CH_2)_3OCO(CH_2)_2COO(CH_2)_3(CF_2)_8F$ Compound C $F(CF_2)_4(CH_2)_2OCO(CH_2)_2COO(CH_2)_2(CF_2)_4F$, $C_4F_9(CH_2)_2OCO(CH_2)_2COO(CH_2)_2C_4F_9$, $C_6F_{13}(CH_2)_2OCO(CH_2)_2COO(CH_2)_2C_6F_{13}$, $C_8F_{17}(CH_2)_2OCO(CH_2)_2COO(CH_2)_2C_{10}F_{21}$, $C_{10}F_{21}(CH_2)_2OCO(CH_2)_2COO(CH_2)_2C_{10}F_{21}$, $C_8F_{17}(CH_2)_2OCO(CH_2)_2COO(CH_2)_2C_{12}F_{25}$, $C_{10}F_{21}(CH_2)_2OCO(CH_2)_2COO(CH_2)_2C_{12}F_{25}$, $C_{12}F_{25}(CH_2)_2OCO(CH_2)_2COO(CH_2)_2C_{12}F_{25}$, $C_6F_{13}(CH_2)_2OCOCH_2CH(CH_3)COO(CH_2)_2C_6F_{13}$,
$C_6F_{13}(CH_2)_2OCOCH_2CH(C_2H_5)COO(CH_2)_2C_6F_{13}$,
$C_6F_{13}(CH_2)_2OCOCH_2CH(C_3H_7)COO(CH_2)_2C_6F_{13}$,
$C_8F_{17}(CH_2)_2OCOCH_2CH(CH_3)COO(CH_2)_2C_8F_{17}$,
$C_8F_{17}(CH_2)_2OCOCH_2CH(C_2H_5)COO(CH_2)_2C_8F_{17}$,
$C_8F_{17}(CH_2)_2OCOCH_2CH(C_3H_7)COO(CH_2)_2C_8F_{17}$,
$C_{10}F_{21}(CH_2)_2OCOCH_2CH(CH_3)COO(CH_2)_2C_{10}F_{21}$,
$C_{10}F_{21}(CH_2)_2OCOCH_2CH(C_2H_5)COO(CH_2)_2C_{10}F_{21}$,
$C_{10}F_{21}(CH_2)_2OCOCH_2CH(C_3H_7)COO(CH_2)_2C_{10}F_{21}$,
$C_{12}F_{25}(CH_2)_2OCOCH_2CH(CH_3)COO(CH_2)_2C_{12}F_{25}$,
$C_6F_{13}SO_2N(CH_3)(CH_2)_2OCO(CH_2)_2COO(CH_2)_2N(CH_3)SO_2C_6F_{13}$,
$C_6F_{13}SO_2N(C_2H_5)(CH_2)_2OCO(CH_2)_2COO(CH_2)_2N(C_2H_5)SO_2C_6F_{13}$,
$C_8F_7SO_2N(CH_3)(CH_2)_2OCO(CH_2)_2COO(CH_2)_2N(CH_3)SO_2C_8F_{17}$,
$C_8F_{17}SO_2N(C_2H_5)(CH_2)_2OCO(CH_2)_2COO(CH_2)_2N(C_2H_5)SO_2C_8F_{17}$,
$C_8F_{17}SO_2N(C_3H_7)(CH_2)_2OCO(CH_2)_2COO(CH_2)_2N(C_3H_7)SO_2C_8F_{17}$,
$C_8F_{17}SO_2N(CH_3)(CH_2)_2OCO(CH_2)_2COO(CH_2)_2N(CH_3)SO_2C_{10}F_{21}$,
$C_8F_{17}SO_2N(C_2H_5)(CH_2)_2OCO(CH_2)_2COO(CH_2)_2N(C_2H_5)SO_2C_{10}F_{21}$,
$C_8F_{17}SO_2N(C_3H_7)(CH_2)_2OCO(CH_2)_2COO(CH_2)_2N(C_3H_7)SO_2C_{10}F_{21}$,
$C_{10}F_{21}SO_2N(CH_3)(CH_2)_2OCO(CH_2)_2COO(CH_2)_2N(CH_3)SO_2C_{10}F_{21}$,
$C_{10}F_{21}SO_2N(C_2H_5)(CH_2)_2OCO(CH_2)_2COO(CH_2)_2N(C_2H_5)SO_2C_{10}F_{21}$,
$C_{10}F_{21}SO_2N(C_3H_7)(CH_2)_2OCO(CH_2)_2COO(CH_2)_2N(C_3H_7)SO_2C_{10}F_{21}$,
$C_6F_{13}SO_2N(C_2H_5)(CH_2)_2OCOCH_2CH(CH_3)COO(CH_2)_2N(C_2H_5)SO_2C_6F_{13}$,
$C_8F_{17}SO_2N(C_2H_5)(C_2H_5)_2OCOCH_2CH(CH_3)COO(CH_2)_2N(C_2H_5)SO_2C_8F_{17}$,
$C_8F_{17}SO_2N(C_2H_5)(CH_2)_2OCOCH_2CH(C_2H_5)COO(CH_2)_2N(C_2H_5)SO_2C_8F_{17}$,
$C_8F_{17}SO_2N(C_2H_5)(CH_2)_2OCOCH_2CH(C_3H_7)COO(CH_2)_2N(C_2H_5)SO_2C_8F_{17}$,
$C_{10}F_{21}SO_2N(CH_3)(CH_2)_2OCOCH_2CH(CH_3)COO(CH_2)_2N(CH_3)SO_2C_{10}F_{21}$.

The compound 1 of the present invention can be produced by e.g. a known or well known esterification reaction or ester exchange reaction. With respect to an esterification reaction as an example, the compound 1 can be produced by reacting an acid component of the following compound 3, 4 or 5 with an alcohol component of at least one type of the following compound 2. Here, the compound 3 is succinic acid or its derivative; the compound 4 is succinic anhydride or its derivative; and the compound 5 is succinic dihalide or its derivative.

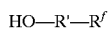 HO—R'—R$^f$  Formula 2

 HOCOCHR$^1$CH$_2$COOH  Formula 3

 O(COCHR$^1$CH$_2$CO)  Formula 4

 XCOCHR$^1$CH$_2$COX  Formula 5

In the compound 2, R' is a $C_{1-4}$ alkylene group or —R$^4$—NR$^5$—SO$_2$— (wherein R$^4$ is a $C_{1-4}$ alkylene group, and R$^5$ is a $C_{1-4}$ alkyl group; and R$^4$ bonds to the oxygen atom), and R$^f$ is a $C_{2-22}$ polyfluoroalkyl group, and in the compounds 3 to 5, R$^1$ is a hydrogen atom or a $C_{1-10}$ alkyl group, and X is a chlorine atom, a bromine atom or an iodine atom.

Now, as a typical example, an acid esterification reaction wherein the compound 2 and the compound 3 are reacted, will be described.

The reaction to form the compound 1 is preferably carried out by a usual acid esterification reaction. The operation, conditions, means, apparatus, etc. for the acid esterification reaction are not particularly limited, and the reaction system may be any of a batch system, a semicontinuous system and a continuous system.

The reaction temperature for the acid esterification reaction is preferably from 0 to 130° C., particularly preferably from 40 to 120° C. As the reaction pressure, it is possible to employ normal pressure, reduced pressure, ambient pressure or elevated pressure. The reaction time is preferably from 3 to 30 hours, although it depends also on the reaction temperature, etc.

Further, the acid esterification reaction is an equilibrium reaction, and it is preferred to let the reaction proceed in a desired direction by separating and removing by-product water out of the reaction system. Accordingly, it is preferred to employ conditions, operation, etc. whereby by-product water can be separated and removed out of the reaction system.

The acid esterification reaction may be carried out in the presence of a catalyst. As such a catalyst, an inorganic strong acid such as sulfuric acid, nitric acid or hydrochloric acid, an organic strong acid such as sulfonic acid or a carboxylic acid, or an alkoxide of a metal such as aluminum or titanium, may, for example, be mentioned. Particularly preferred is p-toluene sulfonic acid, sulfuric acid or hydrochloric acid. The amount of the catalyst is preferably from 0.01 to 0.2 mol per mol of the compound 2.

The acid esterification reaction can be carried out by using a solvent or without using a solvent. In a case where a solvent is to be used, it is preferred to employ a solvent which has no active hydrogen and has a boiling point higher than water or a solvent which is azeotropic with water, taking into consideration that the reaction is a dehydration reaction. As a preferred solvent, toluene or ethyl methyl ketone, may, for example, be mentioned. The amount of the solvent is preferably adjusted so that the concentration of the reactants will be from 10 to 80 mass %.

Further, in the reaction, an amine may be employed as an acid-removing agent. As a preferred acid-removing agent, pyridine, triethylamine or N,N-dimethylaniline, may, for example, be mentioned. The amount of the acid removing agent is preferably from 0 to 4 equivalents to the compound 2.

Further, the reaction employing the compound 4, the reaction employing the compound 5 or the ester exchange reaction, can be carried out in the same manner as the above acid esterification reaction, from the viewpoint that it is an equilibrium reaction wherein water, hydrogen halide or an alcohol is produced as a by-product.

The compound 1 obtained by the above reaction may be subjected to purification as the case requires.

The fluorine-containing compound of the present invention can be used as an additive irrespective of the ionic nature of the main agent of e.g. a water and oil repellent, and particularly when it is added to a water and oil repellent, it can provide dry soil resistance.

In the present invention, the polymer (A) having fluorine atoms is a polymer comprising polymerized units of a polymerizable monomer having fluorine atoms. The polymerizable monomer having fluorine atoms, may, for example, be tetrafluoroethylene, trifluorochloroethylene, hexafluoropropylene, vinyl fluoride, or a (meth)acrylate having a $R^f$ group. In this specification, acrylic acid and methacrylic acid are generally referred to as (meth)acrylic acid, and an expression such as a (meth)acrylate has a similar meaning. Further, the (meth)acrylate having a $R^f$ group is meant for a compound wherein the $R^f$ group is present in the alcohol residue portion of a (meth)acrylate.

The polymer (A) is preferably a polymer which essentially contains polymerized units of a (meth)acrylate having a $R^f$ group, and it is preferably a polymer comprising polymerized units of a (meth)acrylate having a $R^f$ group and polymerized units of a polymerizable monomer other than such a (meth)acrylate.

As the (meth)acrylate having a $R^f$ group, a compound represented by the following formula 2, is preferred. In the formula 2, Q is a bivalent organic group, and $R^8$ is a hydrogen atom or a methyl group.

$$R^{f8}\text{—Q—OCOCR}^8\text{=CH}_2 \qquad \text{Formula 2}$$

In the formula 2, $R^{f8}$ is preferably a $R^f$ group containing no etheric oxygen atom, particularly preferably a perfluoroalkyl group. Especially, a group represented by $F(CF_2)_n$— (wherein n is an integer of from 1 to 16, preferably an integer of from 4 to 16, particularly preferably an integer of from 6 to 12) is preferred.

In the formula 2, Q is preferably —$(CH_2)_{p+q}$—, —$(CH_2)_p CONH(CH_2)_q$—, —$(CH_2)_p OCONH(CH_2)_q$—, —$(CH_2)_p SO_2NR^{11}(CH_2)_q$—, —$(CH_2)_p NHCONH(CH_2)_q$— or —$(CH_2)_p CH(OH)$—$(CH_2)_q$—. Here, $R^{11}$ is a hydrogen atom or an alkyl group. Further, p and q are integers of at least 0, and p+q is an integer of from 1 to 22. Among them, Q is preferably —$(CH_2)_{p+q}$—, —$(CH_2)_p CONH(CH_2)_q$— or —$(CH_2)_p SO_2NR^{11}(CH_2)_q$—, wherein q is an integer of at least 2, and p+q is from 2 to 6, particularly preferably —$(CH_2)_{p+q}$— wherein p+q is from 2 to 6, i.e. from an ethylene group to a hexamethylene group. It is preferred that fluorine atoms are bonded to the carbon atom of $R^f$ which is bonded to Q.

The following compounds may be mentioned as the (meth)acrylate having a $R^f$ group. Here, $R^9$ represents a hydrogen atom or a methyl group.

$CF_3(CF_2)_3 CH_2 OCOCR^9\text{=}CH_2$,
$CF_3(CF_2)_4 CH_2 OCOCR^9\text{=}CH_2$,
$CF_3(CF_2)_5 CH_2 CH_2 OCOCR^9\text{=}CH_2$,
$CF_2 H(CF_2)_5 CH_2 OCOCR^9\text{=}CH_2$,
$CF_2 H(CF_2)_7 CH_2 OCOCR^9\text{=}CH_2$,
$CF_2 H(CF_2)_9 CH_2 OCOCR^9\text{=}CH_2$,
$CF_2 H(CF_2)_7 CH_2 CH_2 OCOCR^9\text{=}CH_2$,
$CF_3(CF_2)_7 CH_2 CH_2 CH_2 OCOCR^9\text{=}CH_2$,
$CF_3(CF_2)_7 CH_2 CH_2 OCOCR^9\text{=}CH_2$,
$CF_3(CF_2)_9 CH_2 CH_2 OCOCR^9\text{=}CH_2$,
$CF_3(CF_2)_{11} CH_2 CH_2 OCOCR^9\text{=}CH_2$,
$CF_3(CF_2)_{13} CH_2 CH_2 OCOCR^9\text{=}CH_2$,
$CF_3(CF_2)_{15} CH_2 CH_2 OCOCR^9\text{=}CH_2$,
$(CF_3)_2 CF(CF_2)_4 CH_2 CH_2 OCOCR^9\text{=}CH_2$,
$(CF_3)_2 CF(CF_2)_6 CH_2 CH_2 OCOCR^9\text{=}CH_2$,
$(CF_3)_2 CF(CF_2)_8 CH_2 CH_2 OCOCR^9\text{=}CH_2$,
$CF_3(CF_2)_7 SO_2 N(C_3 H_7)CH_2 CH_2 OCOCR^9\text{=}CH_2$,
$CF_3(CF_2)_7 (CH_2)_4 COCR^9\text{=}CH_2$,
$CF_3(CF_2)_7 SO_2 N(CH_3)CH_2 CH_2 OCOCR^9\text{=}CH_2$,
$CF_3(CF_2)_7 SO_2 N(C_2 H_5)CH_2 CH_2 OCOCR^9\text{=}CH_2$,
$CF_3(CF_2)_7 CONHCH_2 CH_2 OCOCR^9\text{=}CH_2$,
$(CF_3)_2 CF(CF_2)_5 (CH_2)_3 OCOCR^9\text{=}CH_2$,
$(CF_3)_2 CF(CF_2)_5 CH_2 CH(OCOCH_3)OCR^9\text{=}CH_2$,
$(CF_3)_2 CF(CF_2)_5 CH_2 CH(OH)CH_2 OCOCR^9\text{=}CH_2$,
$(CF_3)_2 CF(CF_2)_7 CH_2 CH(OH)CH_2 OCOCR^9\text{=}CH_2$,
$CF_3(CF_2)_8 CH_2 CH_2 OCOCR^9\text{=}CH_2$,
$CF_3(CF_2)_8 CONHCH_2 CH_2 OCOCR^9\text{=}CH_2$.

The polymer (A) is preferably a polymer comprising one or more types of polymerized units of (meth)acrylates having $R^f$ groups. In a case where it comprises at least two types of such polymerized units, it is preferred that it comprises at least two types of polymerized-units of (meth)acrylates having $R^f$ groups having different carbon numbers.

In the present invention, the polymer (A) is preferably a polymer obtained by polymerizing only a (meth)acrylate having a $R^f$ group, or a copolymer obtained by polymerizing a (meth)acrylate having a $R^f$ group with a polymerizable monomer other than the (meth)acrylate having a $R^f$ group (hereinafter referred to as other monomer).

As such other monomer, a known or well known polymerizable monomer may be mentioned, and a polymerizable monomer having one or two polymerizable unsaturated groups, is preferred. As such other monomer, particularly preferred is one essentially comprising the following polymerizable monomer ($a^1$) and/or the following polymerizable monomer ($a^2$). Further, as other monomer, preferred is a case where both the polymerizable monomer ($a^1$) and the polymerizable monomer ($a^2$) are essentially required, or a case where only the polymerizable monomer ($a^2$) is essentially required.

Polymerizable monomer ($a^1$): at least one polymerizable monomer selected from alkyl (meth)acrylates wherein the carbon number of the alkyl group moiety is from 1 to 20.

Polymerizable monomer ($a^2$): at least one polymerizable monomer selected from an olefin, a vinyl halide, a vinylidene halide, a vinyl carboxylate, styrene, a substituted styrene, a (meth)acrylamide, an N-substituted (meth)acrylamide, an alkyl vinyl ether, a (substituted alkyl)vinyl ether, a vinyl alkyl ketone, a diene, glycidyl (meth)acrylate, aziridinyl (meth)acrylate, a substituted alkyl (meth)acrylate, a hydroxyalkyl (meth)acrylate, a hydroxyl group terminal polyoxyalkylene (meth)acrylate, an alkoxy group terminal polyoxyalkylene (meth)acrylate, a polyoxyalkylene di(meth)acrylate, a polysiloxane group-containing (meth)acrylate, triallyl cyanurate, allyl glycidyl ether, allyl carboxylate, N-vinylcarbazole, N-methyl maleimide, maleic anhydride, a monoalkyl maleate, a dialkyl maleate, and a (meth)acrylate having a blocked isocyanate group.

The carbon number of the alkyl group moiety in the polymerizable monomer ($a^1$) is from 1 to 20. The alkyl group may have a linear, branched or cyclic structure, or a structure partially having a cyclic structure. The polymerizable monomer ($a^1$) may be a combination of two or more types, and in the case of a combination of two or more types, it may be composed of two or more types differing in the structure of the alkyl group moieties.

The polymerizable monomer ($a^1$) is preferably a $C_{1-18}$ alkyl (meth)acrylate, wherein the alkyl group moiety has a linear or branched structure, particularly preferably methyl (meth)acrylate, stearyl (meth)acrylate or 2-ethylhexyl (meth)acrylate.

As the polymerizable monomer ($a^2$), ethylene, vinyl chloride, vinylidene chloride, vinylidene fluoride, vinyl acetate, styrene, α-methylstyrene, p-methylstyrene, glycidyl (meth)acrylate, (meth)acrylamide, N,N-dimethyl (meth) acrylamide, diacetone (meth)acrylamide, methylol-modified diacetone (meth)acrylamide, N-methylol-modified (meth) acrylamide, a vinyl alkyl ether, a halogenated alkyl vinyl ether, a vinyl alkyl ketone, butadiene, isoprene, chloroprene, aziridinylethyl (meth)acrylate, benzyl (meth)acrylate, aziridinyl (meth)acrylate, 2-hydroxyethyl (meth)acrylate, a hydroxyl group terminal polyoxyalkylene (meth)acrylate, a methoxy group terminal polyoxyalkylene (meth)acrylate, a 2-ethylhexylpolyoxyalkylene (meth)acrylate, a polyoxyalkylene di(meth)acrylate, a (meth)acrylate having a polysiloxane, triallyl cyanurate, allyl glycidyl ether, allyl acetate, N-vinylcarbazole, maleimide, n-methylmaleimide or (2-dimethylamino)ethyl (meth)acrylate may, for example, be preferred.

Here, a (meth)acrylate having a blocked isocyanate, is a (meth)acrylate having at least one blocked isocyanate group, and it is preferably a compound having a structure wherein an isocyanate group of a (meth)acrylate having the isocyanate group is blocked with a blocking agent.

Specific examples of the (meth)acrylate having a blocked isocyanate group may be a compound having an isocyanate group of 2-isocyanate ethyl (meth)acrylate blocked with methyl ethyl ketoxime, a compound having an isocyanate group of 2-isocyanate ethyl (meth)acrylate blocked with ε-caprolactam, a compound having an isocyanate group of a 1:1 (molar ratio) reaction product of isophorone diisocyanate with 2-hydroxyethyl (meth)acrylate, blocked with methyl ethyl ketoxime, a compound having an isocyanate group of a 1:1 (molar ratio) reaction product of isophorone diisocyanate with 2-hydroxypropyl (meth)acrylate, blocked with methyl ethyl ketoxime, or a compound having a 1:1 (molar ratio) reaction product of norbornane diisocyanate with 2-hydroxyethyl (meth)acrylate, blocked with methyl ethyl ketoxime. Two or more types of polymerizable monomers ($a^2$) may be used in combination.

As a method to obtain the polymer (A), a known or well known polymerization method, such as bulk polymerization, suspension polymerization, emulsion polymerization, radiation polymerization, photo polymerization or solution polymerization, may be employed. The solvent in the solution polymerization may, for example, be a ketone such as acetone, methyl ethyl ketone or methyl isobutyl ketone, an ether such as dioxane, diethylene glycol dimethyl ether, tetrahydrofuran, methyl t-butyl ether, dipropylene glycol monomethyl ether, dipropylene glycol or tridipropylene glycol, an alcohol such as ethanol, isopropyl alcohol or n-butanol, a hydrocarbon such as mineral spirit, undecene, toluene, xylene or hexane, an amide such as formamide, dimethylformamide, acetoamide or dimethyl acetamide, a carboxylate such as ethyl acetate, butyl acetate, diethyl malonate or diethyl succinate, or a halogenated hydrocarbon such as pentafluorodichloropropane, tridecafluorohexane or methylene chloride.

Further, in emulsion polymerization and suspension polymerization, a method may be employed wherein a polymerizable monomer and an emulsifier are introduced into a medium comprising water, or a solvent mixture of water with a water-soluble solvent, to emulsify the polymerizable monomer, followed by polymerization, or a method may be employed wherein a polymerizable monomer is dissolved and dispersed in a medium composed of a solvent. As the water-soluble solvent, a water-soluble solvent having a solubility of at least 10 g in 100 g of water, is preferred, and acetone, propylene glycol, dipropylene glycol, tripropylene glycol, dipropylene glycol monomethyl ether or ethylene glycol monomethyl ether, may, for example, be mentioned. Two or more water-soluble solvents may be employed in combination. The amount of the water-soluble solvent is preferably from 0 to 80 mass %, based on the polymer (A).

In a usual case, the polymerization is carried out under the action of a polymerization initiating source. The polymerization initiating source is not particularly limited, and a usual polymerization initiator such as an organic peroxide, an azo compound or a persulfate, or ionizing radiation such as γ-rays, may, for example, be employed. The amount of the polymer (A) in the water and oil repellent composition is preferably from 10 to 30 mass %, particularly preferably from 15 to 30 mass %.

The water and oil repellent composition of the present invention preferably contains a surfactant (C). The surfactant (C) may be added to the system during the polymerization or after the polymerization, preferably during the polymerization. As the surfactant (C), a known non-ionic surfactant having an amine oxide moiety in its molecule, other non-ionic surfactant, a cationic surfactant, an amphoteric surfactant or a polymer surfactant, may, for example, be mentioned. These surfactants may be used alone or in combination as a mixture.

As the surfactant (C), it is preferred to employ a surfactant containing no fluorine atom. Further, as such a surfactant, it is preferred to employ any one of the following surfactants ($C^1$) to ($C^6$).

A nonionic surfactant ($C^1$) comprising a polyoxyalkylene alkyl ether, a nonionic surfactant ($C^2$) comprising a compound containing at least one triple bond, at least one hydroxyl group and at least two oxyalkylene moieties in its molecule, a nonionic surfactant ($C^3$) comprising a block polymer having a polyoxyethylene moiety, and a moiety having at least two oxyalkylenes having a carbon number of at least 3 continuously chained, a nonionic surfactant ($C^4$) having an amine oxide moiety in its molecule, a nonionic surfactant ($C^5$) comprising a polyoxyethylene alkylphenyl ether, and a nonionic surfactant ($C^6$) comprising fatty acid ester of polyethylene glycol.

The amount of the surfactant is preferably from 3 to 10 mass %, based on the polymer (A). If the amount of the surfactant exceeds 10 mass %, the water and oil repellency is likely to deteriorate, and if it is less than 3 mass %, the stability of the emulsion is likely to deteriorate. However, there may be an exception when a polymerizable monomer having a self emulsifying property is used.

The compound 1 contained in the water and oil repellent composition of the present invention may be a mixture of two or more types. In the case of two or more types, it may be a mixture of two or more compounds differing only in the chain length of the $R^f$ group, or a mixture of two or more compounds differing in the structure.

The proportion of the compound 1 contained in the water and oil repellent composition of the present invention is preferably from 0.5 to 20 mass %, particularly preferably from 5 to 20 mass %, based on the polymer (A).

The timing for incorporation of the compound 1 to the composition is not particularly limited. However, a method wherein prior to the polymerization, it is charged at the same time as the polymerizable monomer and emulsified, followed by polymerization, or a method wherein after the polymerization, it is mixed and stirred, may, for example, be mentioned, and the former method is preferred.

Further, the water and oil repellent composition of the present invention may further contain an additive other than the polymer (A) and the compound 1. As such an additive, other polymer blender, other water repellent, an oil repellent, an insecticide, a flame retardant, an antistatic agent, a dye stabilizer, a crease preventing agent or a stain blocker, may, for example, be mentioned.

The water and oil repellent composition of the present invention will be diluted to an optional concentration depending upon the particular purpose or application, and will be applied to an object to be treated. As a method for application to an object to be treated, an optional method may be employed depending upon e.g. the type of the object to be treated or the formulation of the composition. For example, a method of applying it to the surface of the object to be treated by a coating method such as dip coating, followed by drying, may be employed. Further, if necessary, it may be applied together with a suitable crosslinking agent, followed by curing.

The water and oil repellent composition of the present invention imparts not only excellent water and oil repellency but also excellent dry soil resistance to the object to be treated. The object to be treated with the water and oil repellent composition of the present invention is not particularly limited, and it may, for example, be fiber, fiber fabric, glass, paper, wood, leather, wool, asbestos, bricks, cement, metal and its oxide, a porcelain product, or a plastic, and fiber fabric is preferred.

The fiber fabric may, for example, be a fabric of an animal or plant natural fiber such as cotton, hemp, wool or silk, a synthetic fiber such as polyamide, polyester, polyvinyl alcohol, polyacrylonitrile, polyvinyl chloride or polypropylene, a semisynthetic fiber such as rayon or acetate, an inorganic fiber such as glass fiber, carbon fiber or asbestos fiber, or a mixed fiber thereof.

The water and oil repellent composition of the present invention is capable of imparting particularly excellent water and oil repellency and excellent dry soil resistance to animal or plant natural fiber, synthetic fiber or semisynthetic fiber, or a fiber fabric made of such fiber. Namely, it is useful particularly as a water and oil repellent composition for carpets and indoor interiors.

EXAMPLES

Example 1
Preparation Example 1 of the above Compound A

Into a 1 l four-necked flask made of glass and equipped with a stirrer, a thermometer, a dropping funnel and a reflux condenser, 278 g of $F(CF_2)_8(CH_2)_2OH$ (purity: 94%) as an alcohol component, 1.5 g of p-toluenesulfonic acid, 36.5 g of succinic acid as an acid component, and 400 g of toluene were charged and reacted at 107° C. for 12 hours. This was washed with warm water of 80° C., then the solvent was distilled off under reduced pressure, and the obtained compound was washed with methanol and dried under reduced pressure to obtain 290 g of the compound A. The conversion of the alcohol component was 99.5%.

In an IR chart of the obtained compound A, disappearance of a peak attributable to —OH was confirmed. The melting point of the compound A was 66.0° C. Further, the $^1$H-NMR spectrum (CDCl$_3$ solvent, TMS internal standard) was δ[ppm]: 4.25 (4H, t), 2.66 (4H, s), 2.46 (4H, m).

Example 2
Preparation Example 2 of the above Compound A

Into a 1 l four-necked flask made of glass and equipped with a stirrer, a thermometer, a dropping funnel and a reflux condenser, 675 g of $F(CF_2)_8(CH_2)_2OH$ (purity: 94%) as an alcohol component, 6.76 g of p-toluenesulfonic acid, and 64.88 g of succinic anhydride as an acid component, were charged and reacted at 110° C. for 3 hours and then, reacted for 12 hours under a reduced pressure of 5.3 kPa. Then, washing was carried out at 80° C. with warm water, and the obtained compound was dried under reduced pressure, then further washed with methanol and dried under reduced pressure to obtain 620 g of the compound A. The conversion of the alcohol component was 99.3%.

In an IR chart of the obtained compound A, disappearance of a peak attributable to —OH was confirmed. The melting point and the $^1$H-NMR spectrum values of the compound A were the same as in Example 1.

Example 3
Preparation Example of the Following Compound B

Compound B: $F(CF_2)_a(CH_2)_2OCO(CH_2)_2COO(CH_2)_2(CF_2)_aF$ (wherein a is an even number of from 6 to 22, and the average value of a is 9).

Into a 1 l four-necked flask made of glass and equipped with a stirrer, a thermometer, a dropping funnel and a reflux condenser, 675 g of $F(CF_2)_a(CH_2)_2OH$ (wherein a is an even number of from 6 to 22, and the average value of a is 9, purity: 94%) as an alcohol component, 6.76 g of p-toluenesulfonic acid, 125 g of triethylamine and 95.64 g of succinic acid dichloride as an acid component, were charged, stirred at 110° C. for 3 hours and then reacted for 3 hours under a reduced pressure of 5.3 kPa. Then, in the same manner as in Example 2, washing and drying were carried out to obtain 600 g of the compound B. The conversion of the alcohol component was 99.3%.

In an IR chart of the obtained compound B, disappearance of a peak attributable to —OH was confirmed. The melting point of the compound B was 66.7° C. Further, the $^1$H-NMR spectrum (CDCl$_3$ solvent, TMS internal standard) was δ[ppm]: 4.25 (4H, t), 2.66 (4H, s), 2.46 (4H, m).

Example 4
Preparation Example of the above Compound C

Into a 1 l four-necked flask made of glass and equipped with a stirrer, a thermometer, a dropping funnel and a reflux condenser, 675 g of $F(CF_2)_8(CH_2)_3OH$ (purity: 94%) as an alcohol component, 6.96 g of p-toluenesulfonic acid, and 64.88 g of succinic acid as an acid component, were charged, stirred at 108° C. for 3 hours and then reacted for 16 hours under a reduced pressure of 5.3 kPa. Then, in the same manner as in Example 2, washing and drying were carried out to obtain 620 g of the compound C. The conversion of the alcohol component was 99.0%.

In an IR chart of the obtained compound C, disappearance of a peak attributable to —OH was confirmed. The melting point of the compound C was 63.5° C. Further, the $^1$H-NMR spectrum (CDCl$_3$ solvent, TMS internal standard) was δ[ppm]: 4.28 (4H, t), 2.67 (4H, s), 2.20 (4H, t), 2.03 (4H, m).

Example 5
Preparation Example of the Following Compound D

Compound D: $F(CF_2)_bSO_2N(CH_3)(CH_2)_2OCO(CH_2)_2COO(CH_2)_2N(CF_3)SO_2(CF_2)_bF$ (wherein b is an even number of from 6 to 22, and the average value of b is 9).

Into a 2 l four-necked flask made of glass and equipped with a stirrer, a thermometer, a dropping funnel and a reflux condenser, 111.4 g of $F(CF_2)_bSO_2N(CH_3)(CH_2)_2OH$ (wherein b is an even number of from 6 to 22, and the average value of b is 9, purity: 94%) as an alcohol component, 10.0 g of succinic anhydride as an acid component, 867 g of toluene and 0.92 g of sulfuric acid, were charged and reacted at 110° C. for 10 hours. Then, in the same manner as in Example 2, washing and drying were carried out to obtain 111 g of the compound D. The conversion of the alcohol component was 99.3%.

In an IR chart of the obtained compound D, disappearance of a peak attributable to —OH was confirmed. The melting point of the compound D was 160.9° C. Further, the $^1$H-NMR spectrum (CDCl$_3$ solvent, TMS internal standard) was δ[ppm]: 4.22–4.42 (4H, m), 3.38–3.94 (4H, m), 3.15 (6H, s), 2.69 (4H, s).

Example 6
Preparation Example of the Following Compound E

Compound E: $F(CF_2)_dSO_2N(C_2H_5)(CH_2)_2OCO(CH_2)_2COO(CH_2)_2N(C_2H_5)SO_2(CF_2)_d$ (wherein d is an even number of from 6 to 22, and the average value of b is 9).

Into a 2 l four-necked flask made of glass and equipped with a stirrer, a thermometer, a dropping funnel and a reflux condenser, 262 g of $F(CF_2)_dSO_2N(C_2H_5)(CH_2)_2OH$ (wherein d is an even number of from 6 to 22, and the average value of d is 9, purity: 94%) as an alcohol component, 22.94 g of succinic anhydride as an acid component, 1127 g of toluene and 1.84 g of sulfuric acid, were charged and reacted at 10° C. for 10 hours. Then, in the same manner as in Example 2, washing and drying were carried out to obtain 180 g of the compound E. The conversion of the alcohol component was 99.3%.

In an IR chart of the obtained compound E, disappearance of a peak attributable to —OH was confirmed. The melting point of the compound E was 85.9° C. Further, the $^1$H-NMR spectrum (CDCl$_3$ solvent, TMS internal standard) was δ[ppm]: 4.29 (4H, t), 3.53–3.85 (8H, m), 2.68 (4H, s), 1.29 (6H, t).

Example 7
Evaluation of Dry Soil Resistance

A composition comprising 167 g of a perfluoroalkylethyl acrylate [mixture of $CF_3(CF_2)_vCH_2CH_2COCH=CH_2$, wherein v is from 5 to 15 (average value: 8)], 30 g of the compound A, 46.2 g of stearyl acrylate, 5.1 g of N-methylol acrylamide, 0.77 g of stearyl mercaptan, 10.3 g of (polyoxyethylene)oleyl ether having a terminal hydroxyl group, 5.1 g of a surfactant represented by the following formula 6 (wherein x is an integer of from 0 to 10, y is an integer of from 0 to 10, and the average value of x+y is 10), 5.1 g of polyoxyethylene secondary alcohol ether having a terminal hydroxyl group ("BT-12", tradename, manufactured by Nikko Chemicals Co., Ltd., the carbon number of the secondary alcohol is from 12 to 14, and the number of oxyethylene chains is 12), 130 g of tripropylene glycol and 350 g of deionized water, was stirred at 50° C. for 30 minutes. While maintaining the composition at a temperature of from 40 to 50° C., it was emulsified under 40 MPa by means of a high pressure emulsifier manufactured by Manton Gaulin Company. The particle size of the emulsion after the emulsification was 0.18 μm.

Formula 6

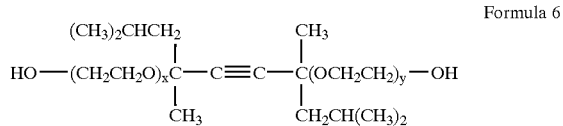

Then, this emulsion was transferred to a 1 l autoclave made of glass, and 0.5 g of azobis (dimethyleneisobutylamidine) hydrochloride was added. Then, the autoclave was flushed with nitrogen. Then, 38.5 g of vinyl chloride was added, and the temperature was raised to 60° C. with stirring, and polymerization was carried out for 15 hours to obtain a milky white emulsion containing a polymer having an average molecular weight of 70,000. The solid content concentration of the emulsion was 38.5 mass %, and the average particle size was 0.09 μm.

The emulsion was diluted with water so that the solid content concentration became 20 mass %, to obtain the emulsion stock solution. The obtained emulsion stock solution was diluted so that the proportion of the emulsion stock solution to water became 2 mass % to obtain a treating solution, whereby dry soil resistance (anti-dry soil property) was measured.

Into the above treating solution, a nylon knitted cloth was immersed and squeezed between a pair of rubber rollers to a wet pickup of 60 mass %. Then, it was dried at 110° C. for 90 seconds and further heat-treated at 170° C. for 60 seconds, whereupon with respect to the treated cloth, evaluation of the property was carried out under the following standards. As a result, the dry soil resistance was 4.9.

Dry Soil Resistance

A dry soil was prepared by the components shown in Table 1, and 1.25 g of the dry soil, ten sheets of the above-mentioned treated cloth (5 cm×5 cm) and ten rubber balls having a diameter of 1.5 cm, were put into a polyvinyl bag of 30 cm×40 cm, and nitrogen was sealed in. This bag was vigorously shaked for 5 minutes, whereupon excess dry soil on the surface of the treated cloth was removed by an electric vacuum cleaner, and the brightness of the surface of the treated cloth was measured by a color difference meter. Then, the dry soil resistance was evaluated by calculating the soiled degree by the formula, soiled degree=$L^0$–L (where $L^0$: brightness before soiling, and L: brightness after soiling). Here, by this evaluation, the smaller the numerical value, the higher the performance.

TABLE 1

| Components | Mass ratio |
| --- | --- |
| Peat moss | 40 |
| Portland Cement | 17 |
| Kaolin clay | 17 |
| Silica | 17 |
| Carbon black | 0.1 |
| Iron oxide for ferrite | 0.15 |
| Nujol | 8.75 |

The entire disclosure of Japanese Patent Application No. 2000-54069 filed on Feb. 29, 2000 including specification, claims and summary are incorporated herein by reference in its entirety.

What is claimed is:

1. A water and oil repellent composition comprising:
   polymer (A) comprising polymerized units of a (meth) acrylate having a polyfluoroalkyl group and
   (B) a fluorine-containing compound of the following formula 1:

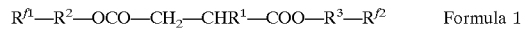

wherein each of $R^{f1}$ and $R^{f2}$ which are independent of each other, is a $C_{2-22}$ polyfluoroalkyl group;
$R^1$ is a hydrogen atom or a $C_{1-10}$ alkyl group; and
each of $R^2$ and $R^3$ which are independent of each other, is a $C_{1-4}$ alkylene group or
—$R^4$—$NR^5$—$SO_2$—, wherein $R^4$ is a $C_{1-4}$ alkylene group, and $R_5$ is a $C_{1-4}$ alkyl group.

2. The water and oil repellent composition according to claim 1, wherein the polymer (A) is a polymer comprising polymerized units of an alkyl (meth)acrylate wherein the alkyl moiety has a carbon number of from 1 to 20.

3. A method for fiber treatment comprising contacting a fiber with a water and oil repellent composition according to claim 1.

4. The water and oil repellant composition according to claim 1, wherein in (B) $R^{f1}$ and $R^{f2}$ are each independently selected from the group consisting of $F(CF_2)_2—$, $F(CF_2)_3—$, $F(CF_2)_4—$, $F(CF_2)_5—$, $F(CF_2)_6—$, $F(CF_2)_8—$, $F(CF_2)_9—$, $F(CF_2)_{10}—$, $F(CF_2)_{12}—$, $F(CF_2)_{13}—$, $F(CF_2)_{14}—$, $F(CF_2)_{16}—$, $H(CF_2)_8—$, $(CF_3)_2CF(CF_2)_6—$, $(CF_3)_2CF(CF_2)_8—$, $Cl(CF_2)_8—$, $F(CF_2)_3OCF(CF_3)—$, $F(CF_2)_2(CF_2OCF(CF_3))_2—$ and $F(CF_2)_3OCF(CF_3)O(CF_2)_2—$.

5. The water and oil repellant composition according to claim 1, wherein (B) is selected from the group consisting of $F(CF_2)_8(CH_2)_2OCO(CH_2)_2COO(CH_2)_2(CF_2)_8F$,
$F(CF_2)_8(CH_2)_3OCO(CH_2)_2COO(CH_2)_3(CF_2)_8F$,
$F(CF_2)_4(CH_2)_2OCO(CH_2)_2COO(CH_2)_2(CF_2)_4F$,
$C_4F_9(CH_2)_2OCO(CH_2)_2COO(CH_2)_2C_4F_9$,
$C_6F_{13}(CH_2)_2OCO(CH_2)_2COO(CH_2)_2C_6F_{13}$,
$C_8F_{17}(CH_2)_2OCO(CH_2)_2COO(CH_2)_2C_{10}F_{21}$,
$C_{10}F_{21}(CH_2)_2OCO(CH_2)_2COO(CH_2)_2C_{10}F_{21}$,
$C_8F_{17}(CH_2)_2OCO(CH_2)_2COO(CH_2)_2C_{12}F_{25}$,
$C_{10}F_{21}(CH_2)_2OCO(CH_2)_2COO(CH_2)_2C_{12}F_{25}$,
$C_{12}F_{25}(CH_2)_2OCO(CH_2)_2COO(CH_2)_2C_{12}F_{25}$,
$C_6F_{13}(CH_2)_2OCOCH_2CH(CH_3)COO(CH_2)_2C_6F_{13}$,
$C_6F_{13}(CH_2)_2OCOCH_2CH(C_2H_5)COO(CH_2)_2C_6F_{13}$,
$C_6F_{13}(CH_2)_2OCOCH_2CH(C_3H_7)COO(CH_2)_2C_6F_{13}$,
$C_8F_{17}(CH_2)_2OCOCH_2CH(CH_3)COO(CH_2)_2C_8F_{17}$,
$C_8F_{17}(CH_2)_2OCOCH_2CH(C_2H_5)COO(CH_2)_2C_8F_{17}$,
$C_8F_{17}(CH_2)_2OCOCH_2CH(C_3H_7)COO(CH_2)_2C_8F_{17}$,
$C_{10}F_{21}(CH_2)_2OCOCH_2CH(CH_3)COO(CH_2)_2C_{10}F_{21}$,
$C_{10}F_{21}(CH_2)_2OCOCH_2CH(C_2H_5)COO(CH_2)_2C_{10}F_{21}$,
$C_{10}F_{21}(CH_2)_2OCOCH_2CH(C_3H_7)COO(CH_2)_2C_{10}F_{21}$,
$C_{12}F_{25}(CH_2)_2OCOCH_2CH(CH_3)COO(CH_2)_2C_{12}F_{25}$,
$C_6F_{13}SO_2N(CH_3)(CH_2)_2OCO(CH_2)_2COO(CH_2)_2N(CH_3)SO_2C_6F_{13}$,
$C_6F_{13}SO_2N(C_2H_5)(CH_2)_2OCO(CH_2)_2COO(CH_2)_2N(C_2H_5)SO_2C_6F_{13}$,
$C_8F_{17}SO_2N(CH_3)(CH_2)_2OCO(CH_2)_2COO(CH_2)_2N(CH_3)SO_2C_8F_{17}$,
$C_8F_{17}SO_2N(C_2H_5)(CH_2)_2OCO(CH_2)_2COO(CH_2)_2N(C_2H_5)SO_2C_8F_{17}$,
$C_8F_{17}SO_2N(C_3H_7)(CH_2)_2OCO(CH_2)_2COO(CH_2)_2N(C_3H_7)SO_2C_8F_{17}$,
$C_8F_{17}SO_2N(CH_3)(CH_2)_2OCO(CH_2)_2COO(CH_2)_2N(CH_3)SO_2C_{10}F_{21}$,
$C_8F_{17}SO_2N(C_2H_5)(CH_2)_2OCO(CH_2)_2COO(CH_2)_2N(C_2H_5)SO_2C_{10}F_{21}$,
$C_8F_{17}SO_2N(C_3H_7)(CH_2)_2OCO(CH_2)_2COO(CH_2)_2N(C_3H_7)SO_2C_{10}F_{21}$,
$C_{10}F_{21}SO_2N(CH_3)(CH_2)_2OCO(CH_2)_2COO(CH_2)_2N(CH_3)SO_2C_{10}F_{21}$,
$C_{10}F_{21}SO_2N(C_2H_5)(CH_2)_2OCO(CH_2)_2COO(CH_2)_2N(C_2H_5)SO_2C_{10}F_{21}$,
$C_{10}F_{21}SO_2N(C_3H_7)(CH_2)_2OCO(CH_2)_2COO(CH_2)_2N(C_3H_7)SO_2C_{10}F_{21}$,
$C_6F_{13}SO_2N(C_2H_5)(CH_2)_2OCOCH_2CH(CH_3)COO(CH_2)_2N(C_2H_5)SO_2C_6F_{13}$,
$C_8F_{17}SO_2N(C_2H_5)(CH_2)_2OCOCH_2CH(CH_3)COO(CH_2)_2N(C_2H_5)SO_2C_8F_{17}$,
$C_8F_{17}SO_2N(C_2H_5)(CH_2)_2OCOCH_2CH(C_2H_5)COO(CH_2)_2N(C_2H_5)SO_2C_8F_{17}$,
$C_8F_{17}SO_2N(C_2H_5)(CH_2)_2OCOCH_2CH(C_3H_7)COO(CH_2)_2N(C_2H_5)SO_2C_8F_{17}$,
$C_{10}F_{21}SO_2N(CH_3)(CH_2)_2OCOCH_2CH(CH_3)COO(CH_2)_2N(CH_3)SO_2C_{10}F_{21}$, and mixtures thereof.

6. The water and oil repellant composition according to claim 1, wherein said (meth)acrylate containing a polyfluoroalkyl group is selected from the group consisting of $CF_3(CF_2)_2CH_2OCOR^9=CH_2$,
$CF_3(CF_2)_4CH_2OCOCR^9=CH_2$,
$CF_3(CF_2)_5CH_2CH_2OCOCR^9=CH_2$,
$CF_2H(CF_2)_5CH_2OCOCR^9=CH_2$,
$CF_2H(CF_2)_7CH_2OCOCR^9=CH_2$,
$CF_2H(CF_2)_9CH_2OCOCR^9=CH_2$,
$CF_2H(CF_2)_7CH_2CH_2OCOCR^9=CH_2$,
$CF_3(CF_2)_7CH_2CH_2CH_2OCOCR^9=CH_2$,
$CF_3(CF_2)_7CH_2CH_2OCOCR^9=CH_2$,
$CF_3(CF_2)_9CH_2CH_2OCOCR^9=CH_2$,
$CF_3(CF_2)_{11}CH_2CH_2OCOCR^9=CH_2$,
$CF_3(CF_2)_{13}CH_2CH_2OCOCR^9=CH_2$,
$CF_3(CF_2)_{15}CH_2CH_2OCOCR^9=CH_2$,
$(CF_2)_2CF(CF_2)_4CH_2CH_2OCOCR^9=CH_2$,
$(CF_3)_2CF(CF_2)_6CH_2CH_2OCOCR^9=CH_2$,
$(CF_3)_2CF(CF_2)_8CH_2CH_2OCOCR^9=CH_2$,
$CF_3(CF_2)_7SO_2N(C_3H_7)CH_2CH_2OCOCR^9=CH_2$,
$CF_3(CF_2)_7(CH_2)_4OCOCR^9=CH_2$,
$CF_3(CF_2)_7SO_2N(CH_3)CH_2CH_2OCOCR^9=CH_2$,
$CF_3(CF_2)_7SO_2N(C_2H_5)CH_2CH_2OCOCR^9=CH_2$,
$CF_3(CF_2)_7CONHCH_2CH_2OCOCR^9=CH_2$,
$(CF_3)_2CF(CF_2)_5(CH_2)_3OCOCR^9=CH_2$,
$(CF_3)_2CF(CF_2)_5CH_2CH(OCOCH_3)OCR^9=CH_2$,
$(CF_3)_2CF(CF_2)_5CH_2CH(OH)CH_2OCOCR^9=CH_2$,
$(CF_3)_2CF(CF_2)_7CH_2CH(OH)CH_2OCOCR^9=CH_2$,
$CF_3(CF_2)_8CH_2CH_2OCOCR^9=CH_2$,
$CF_3(CF_2)_8CONHCH_2CH_2OCOCR^9=CH_2$, and mixtures thereof.

7. A method of imparting dry soil resistance to a material, which comprises treating a surface of said material with an effective amount of the water and oil repellant composition of claim 1 to impart dry soil resistance thereto.

8. A method of imparting water and oil resistance to a material, which comprises treating a surface of said material with an effective amount of the water and oil repellant composition of claim 1 to impart water and oil resistance thereto.

* * * * *